United States Patent [19]
Wheeler

[11] Patent Number: 5,714,998
[45] Date of Patent: Feb. 3, 1998

[54] VIDEO INSPECTION SYSTEM FOR CONVEYORS

[75] Inventor: Tracy Eugene Wheeler, Terre Haute, Ind.

[73] Assignees: Sony Corporation, Tokyo, Japan; Digital Audio Disc Corporation, Terre Haute, Ind.

[21] Appl. No.: 782,960

[22] Filed: Jan. 13, 1997

[51] Int. Cl.$^6$ .............. H04N 7/18; H04N 9/47; G01N 21/00
[52] U.S. Cl. .............. 348/92; 348/127; 356/237; 382/143
[58] Field of Search .............. 348/86, 88, 92, 348/125, 127, 128, 94, 95, 87, 126; 356/237; 382/143, 141, 145, 149; 250/223 B

[56] References Cited

U.S. PATENT DOCUMENTS

| | | | |
|---|---|---|---|
| 3,894,806 | 7/1975 | Remy et al. | 250/223 B |
| 4,209,802 | 6/1980 | Fogg et al. | 250/223 B |
| 5,256,871 | 10/1993 | Baldwin | 250/223 B |
| 5,305,099 | 4/1994 | Morcos | 348/88 |
| 5,311,304 | 5/1994 | Monno | 348/87 |
| 5,452,080 | 9/1995 | Tomiya | 356/237 |
| 5,532,739 | 7/1996 | Garakani et al. | 348/47 |

*Primary Examiner*—Amelia Au
*Assistant Examiner*—Nhon T. Diep
*Attorney, Agent, or Firm*—Wood, Herron & Evans L.L.P.

[57] ABSTRACT

An inspection system for use with a moving conveyor (20) having a video camera (80) mounted above the conveyor (20) and first and second prisms (60, 62) mounted below the camera (80) but above the part (28) to be inspected. The prisms (60, 62) are oriented to be parallel to two opposite ends (30, 36) of the part to be inspected. Therefore, as the conveyor (20) moves the part (28) below the prisms (60, 62) to an inspection location between the prisms, the camera (80) provides simultaneous images of the ends (30,36) of the part (28) as well the part's upper surface (46).

15 Claims, 3 Drawing Sheets

5,714,998

1

VIDEO INSPECTION SYSTEM FOR CONVEYORS

FIELD OF THE INVENTION

This invention relates to inspection systems and more particularly, to a video inspection booth for conveyors.

BACKGROUND OF THE INVENTION

The inspection of parts for defects in manufacturing and assembly is widely used in industry. Of particular interest are those systems that inspect parts as they move along a conveyor system in the normal process of manufacturing. Further, it is desirable to inspect as many characteristics as possible with a single set up or piece of equipment in the shortest period of time and with minimal disruption to the conveyor operation.

A variety of products are packaged in boxes with different labels on different sides of the packaging, and normally, those labels are inspected for their condition and placement. For example, products, such as compact discs and CD-ROMs, are packaged in thin plastic cases. Generally, each CD case is made from square shaped, clear plastic container and an opposed, mating clear plastic lid. The case is joined or hinged along a common rear end between the container and the lid, and a latch is located on an opposite forward end that is designed to facilitate opening and closing the lid of the case. As part of the packaging process a liner containing printed labels is inserted in the case, and most often, the liner extends across an upper surface below the lid, down the hinged rear end, across the lower surface on the bottom of the container and up the front end with the latch. After the liner is inserted into the case, the CD is then inserted into the case; and the case is carried, lying flat on a conveyor surface or belt to be further processed.

As part of that further processing, often, the case is inspected to determine whether the liner has been properly inserted into the case and has not been crushed by the insertion of the CD or another operation. Generally and preferably, the case is oriented on the conveyor with the hinged end in front leading the motion of the case, and the lid is facing upward. The CD title and main image are located on the inserted label immediately below the lid and therefor, inspecting the lid surface is important. Further, the portions of the liner under the front and rear ends are susceptible to be crushed in the assembly process, and therefor, it is desirable to inspect the front and rear ends of the case.

Historically such inspections took place by manually unloading finished cases from a packed carton, visually inspecting the surfaces and ends of the case and then repacking the cases into the carton. Such an inspection practice has the disadvantages of being tedious, time consuming and substantially increasing the processing time and labor cost of packaging the CD's.

Consequently, there is a need for an inspection system that permits the CD case to be inspected preferably while it is moving on the conveyor. Further, such a system should permit the inspection to occur automatically, without manual labor, and quickly, so that the overall efficiency of the CD packaging process is not compromised.

SUMMARY OF THE INVENTION

The present invention provides a video inspection system which is adapted to be readily connected to a conveyor system and that automatically and efficiently simultaneously inspects the top surface and the leading and trailing edges of an item moving along the conveyor. Therefore, the video inspection system is especially useful for inspecting the condition of an internal liner extending over the upper surface and the front and rear ends of a CD case.

According to the principles of the present invention and in accordance with the preferred embodiments, the inspection system includes a frame adapted to be attached to the conveyor wherein the frame has a video camera mounted thereto above the conveyor. A first prism is mounted to the frame below the camera but above the part so that the part can pass below the first prism. The first prism is mounted parallel to a first end or edge of the part to be inspected. A second prism is also mounted to the frame below the camera but above the part so that the part can also pass below the second prism. The second prism is mounted parallel to a second end or edge of the part to be inspected. Therefore, as the conveyor moves the part below the prisms to an inspection location between the prisms, the camera provides simultaneous images of the ends of the part. Therefore, the inspection system has the advantage of being able to automatically and simultaneously inspect two separate edges or ends of a part while the conveyor is moving. The inspection process takes places with the conveyor moving at full speed and without having to pickup and handle the workpiece. The inspection system has the further advantages of being a static system with no moving parts, of being attachable to the conveyor at any desired location, and of performing the inspection without having to slow down or stop the conveyor.

In one aspect of the invention, the ends of the part to be inspected are on opposite ends of the part and the first and second prisms are oriented to be approximately perpendicular to the direction of conveyor motion. In a further aspect of the invention, when the part is at the inspection location, the camera also provides a simultaneous image of an upper surface of the part, thereby permitting the camera to simultaneously inspect two opposite end and an intermediate surface of the part. Therefore, the inspection system has the further advantage of being able to automatically inspect the top of the CD case simultaneously with the inspection of the opposed leading and trailing edges.

These and other objects and advantages of the present invention will become more readily apparent during the following detailed description taken in conjunction with the drawings herein.

DETAILED DESCRIPTION OF THE INVENTION

Figure 1:
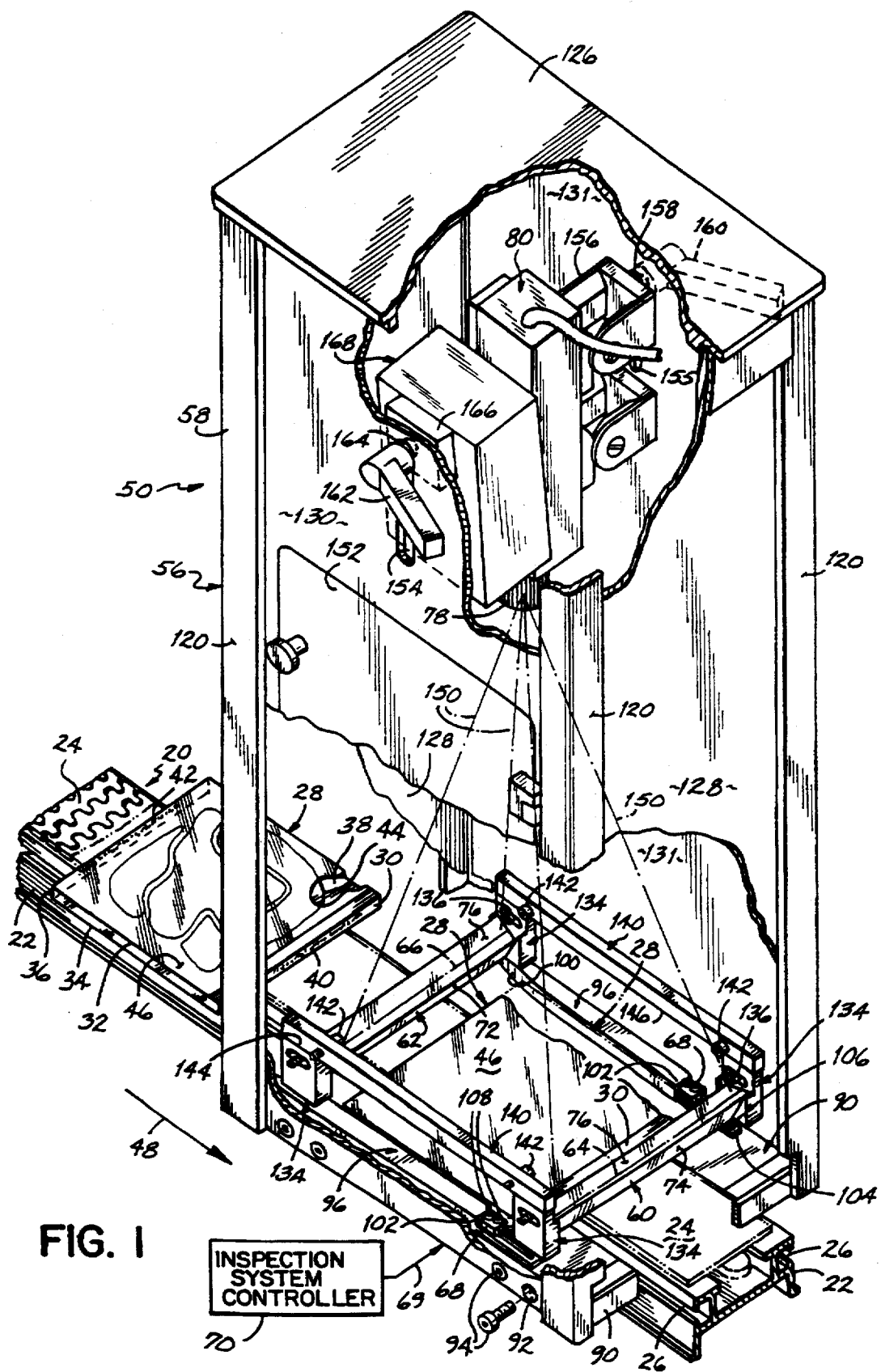
FIG. 1 is a perspective view of the video inspection system in accordance with the principles of the present invention.

Referring to FIG. 1, a conveyor 20 is comprised of opposed side rails 22, which support a moving conveyor belt 24. The side rails 22 are often an extruded aluminum piece which includes a notch 26 sized to accept the head of a bolt or other fastener. A part 28 is supported on the moving belt 24 and may be, for example, a plastic CD case. The case 28 has a planar hinged edge or end wall 30 joining an upper case member 32 to a lower case member 34. The hinge 30 permits the case 28 to be easily opened at an opposite planar edge or end wall 36. As part of the manufacturing process, a liner 38 is inserted into the case 28, and the liner 38 has indicia 40 extending across and visible through the hinged end wall 30 of the case 28. In addition, the liner contains other indicia 42 extending across and visible through the other end wall 36. Further, the label has indicia 44 extending across and visible through an upper surface 46, the upper member 32 of the case 28. The case 28 is moved by the conveyor belt 24 in the direction 48 with the hinged end 30 being a leading edge with respect to the motion of the conveyor 24. As the case 28 is moved by the conveyor 24, the end walls 30, 36 define planes that are generally vertically oriented with respect to the conveyor, perpendicular to the upper surface 42 and also generally perpendicular to the direction of conveyor motion. It is possible in the assembly process, that one or more sides of the liner 38 have become crushed, crumbled, torn, bent, or otherwise mutilated, and it is desirable to detect such defects accurately, quickly, and with minimum variation to the standard conveying process.

The inspection system 50 of the present invention includes a camera cabinet 56 that has a frame 58 attached to the side rails 22 of the conveyor 20. A first prism 60 and a second prism 62 are mounted on the frame 58 such that longitudinal centerlines 64, 66 extend in a direction substantially perpendicular to the direction 48 of the motion of the conveyor belt 24. The prisms 60, 62 are mounted above the conveyor belt 24 such that the case 28 can pass below the prisms without interference. As the conveyor belt 24 moves the case 28 through the cabinet 56, proximity sensors 68, for example, photoelectric sensors, detect the leading edge, that is, the hinge end 30 of the case 28 and produce a signal, via cable 69, to a controller 70. The prisms 60, 62 are oriented such that upon the sensors 68 detecting the case 28, light reflected from the ends 30, 36 of the case enters downwardly directed surfaces 72, is reflected off of reflective surfaces 74 and exits the prisms 60, 62 through upward directed surfaces 76. The light exiting the prisms 60, 62 is preferably directed toward and is within the field of a lens 78 of a video camera 80. The video camera 80 is mounted with its lens 78 directed in a generally vertical downward direction; and the camera 80 is mounted in the cabinet 56, so that its height above the conveyor belt 24 is adjustable. Upon the controller 70 detecting the signal from the sensors 68, the camera is strobed ON and OFF; and the camera 80 provides an electronic image that includes images of the ends 30, 36, as well as an image of the upper surface 46 of the case 28. Therefore, the video inspection system of the present invention is capable of simultaneously inspecting the ends 30, 36 and the upper surface 46 of the case 28 as it is moving along the conveyor 20.

Referring to the frame 58 of the camera cabinet 56 in more detail, identical conveyor mounting brackets 90 forming a lower portion of the frame 58 are mounted on each side of the conveyor 20. Preferably, T-nuts (not shown) are inserted in the slots 26 of the side rails 22 and are aligned with the holes 92 in the mounts 90. Screws 94 or other fasteners are inserted into the holes 92 and threaded into the T-nuts to securely attach the conveyor mounts 90 of the cabinet 56 to the conveyor 20. As will be appreciated, the screws 94 may be loosened, thereby permitting the cabinet 56 to slide with respect to the side rails 22 to either move the cabinet 56 to a new position or remove it completely from the conveyor. Guides 96 are attached to the upper surface of the mounts 90 by screws 97 (FIG. 2) extending from the undersides of the mounts 90 through slots 98 (FIG. 3) and into threaded holes of the guides 96. The slots 98 permit the guides 96 to be moved laterally, that is, side-to-side with respect to the conveyor, so that the guides 96 are separated by a distance equaling the width of the case 28 plus approximately 1 millimeter (1 mm). The ends 100 (FIG. 3) of the guides 96, which receive the case 28 as it moves along the conveyor belt 24 are radiused or flared to provide an opening between the guides 96 that is substantially larger than the width of the case 28. Therefore, the guides function to capture and align the case 28 as it moves along the conveyor belt such that the ends 30, 36 are substantially parallel to the prisms 60, 62.

Figure 2:
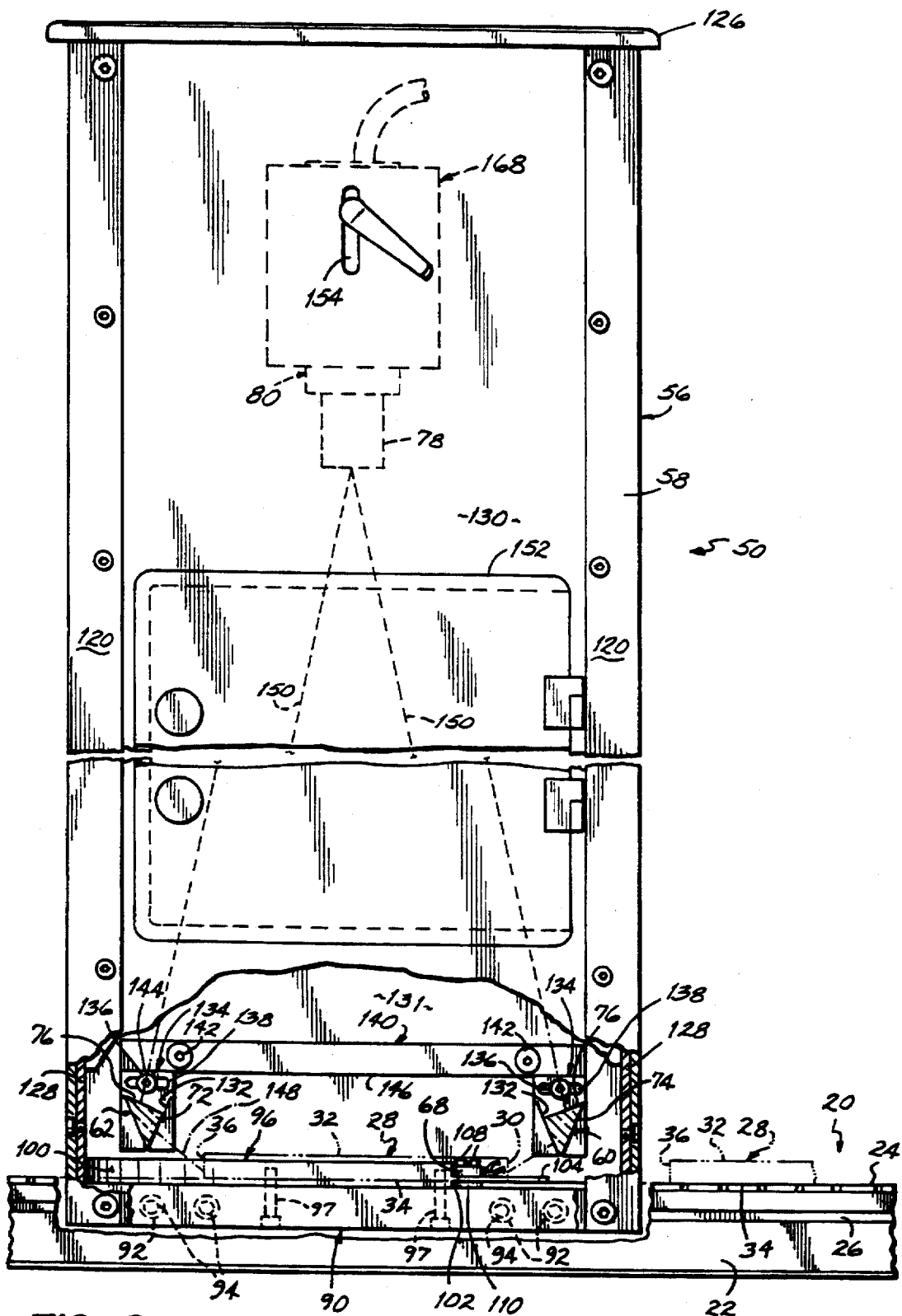
FIG. 2 is a side elevation view of the video inspection system shown in FIG. 1.
Figure 3:
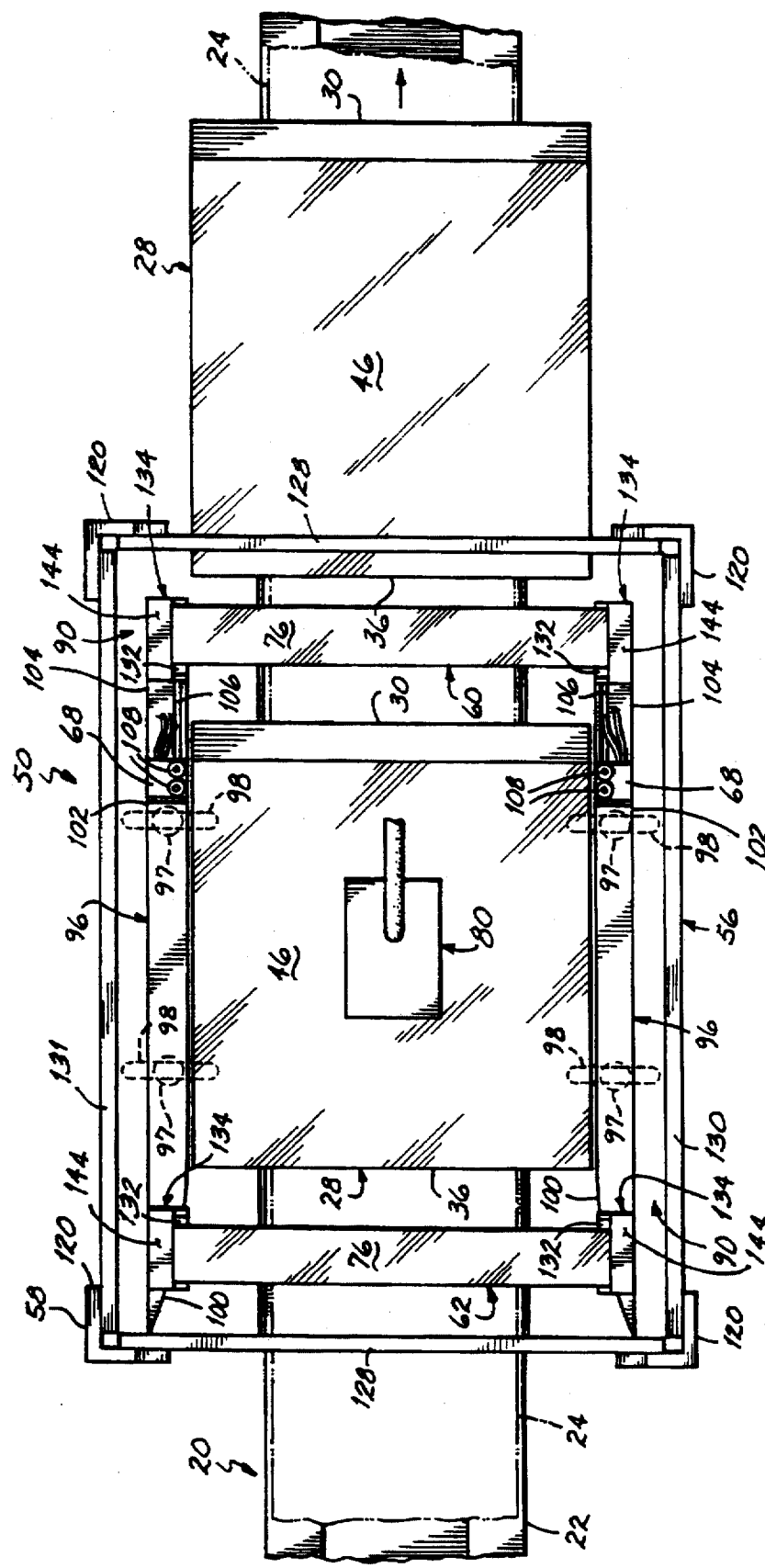
FIG. 3 is a diagrammatic top plan view of the video inspection system shown in FIG. 1 but with the top removed and the camera shown schematically.

Referring to FIGS. 2 and 3, the other ends 102 of the guides 96 are notched from their upper and lower sides to form tongues 104 having longitudinal slots 106 (FIG. 3). The tongues 104 are recessed from the upper surface of the guides 96 to accept the proximity switches 68. Fasteners 108 extend through the proximity switches 68, the slots 106 into threaded holes in plates 110, thereby securing the switches in place. The slots 106 permit the switches to be precisely aligned with the leading edge 30 of the case 28.

As shown in FIGS. 1 and 3, the camera box 56 has four vertically extending corner angles 120, which are also preferably aluminum extrusions. The corner angles 120 are fastened or otherwise rigidly connected at their lower ends to the conveyor mounts 90; and the corner angles 120 are fastened or otherwise rigidly connected at their upper ends to a top or cover 126 of the camera box 56. The camera box 56 preferably includes two opposed side walls 128, which extend from the upper surface of the conveyor mounts 90 to the top cover 126, thereby fully enclosing the sides of the camera box 56. The side walls 128 are preferably identical aluminum plates which are fastened inside the flanges of the corner angles 120.

The camera box 56 further has identical front and rear walls 130, 131, respectively, which are also preferably aluminum plates that are fastened inside the flanges of the corner angles 120. The prisms 60, 62 are mounted at the lower ends of the walls 130, 131. Referring to FIG. 2, the ends of the prisms 60, 62 are supported in generally V-shaped slots 132 formed on the inner directed surfaces of the prism mounts 134. The prism mounts 134 are mounted to the front and rear walls 130, 131 preferably by fasteners, for example, screws 136 that extend through slots 138 and are fastened to respective walls 130, 131. Each of the plates 130, 131 further includes an alignment bar 140, which is secured to its respective plate preferably by fasteners 142. The alignment bar 140 is mounted so that it is approximately parallel with the conveyor 24. The upper surfaces 144 of the respective prism mounts 134 are made to be in sliding contact with a lower surface 146 of the alignment bar 140. The slots 138 permit the prisms mounts and hence the ends the prisms 60, 62 to be adjusted longitudinally with respect to the conveyor. The purpose of the alignment bar 140 is to maintain the prism mounts 134 square with respect to the conveyor 24 as the mounts 134 are adjusted to their desired positions with respect to the ends 30, 36 of the case 28. The prisms 60, 62 are preferably 45° prisms, and the prism mounts 134 are adjusted such that the angle of incidence of light 148 with respect to the reflecting surface 74 is approximately 22.5°. Similarly, the light 150 is reflected from the surface 74 at an angle therewith of approximately 22.5°. Further in the illustrated embodiment, the reflected light 150 also forms an angle with a vertical line of approximately 22.5°.

Referring to FIG. 1, each of the walls 130, 131 also includes an access door 152 hinged to its respective panel. The panels 130, 131 further include at their upper ends generally vertical slots 154, 155, respectively, for mounting equipment within the cabinet. For example, the camera 80 is attached to a mounting bracket 156 that, in turn, is threadedly connected to a shaft 158 extending through slot 155 of wall 131. The outer end of the shaft 158 is attached to a handle 160. Rotating the handle in a first direction loosens the bracket 156 from the wall 131, thereby permitting the camera 80 to be moved in a generally vertical direction inside the cabinet 56. When the camera is located in its desired position, the handle 160 is rotated in the opposite direction to lock or secure the camera in that position. In a similar manner, the handle 162 has a shaft 164 extending through slot 154 of wall 130 into a bracket 166 attached to a light 168. Therefore, rotating the handle 162 in one direction loosens the light 168 so that it may be adjusted in a generally vertical direction within the cabinet 56. Rotating the handle 162 in the opposite direction secures the light 168 in its desired position on the wall 130. The camera 80 is preferably a progressive scan camera, model no. TM 9701 commercially available from Pulnix America, Inc. of Sunnyvale, Calif. The light 168 is preferably a fiber optic light source model no. 1001 commercially available from Fostec Inc. of Auburn, N.Y.

In use, the cabinet 56 is first located and mounted on the conveyor 24 at the desired position. Next, the guides 96 are adjusted such that they locate the case 28 symmetrically about the longitudinal centerline of the conveyor 24. The guides 96 should position the case 28 so that its leading and trailing edges 30, 36, respectively, are parallel to the longitudinal axis 64, 66 of the respective prisms 60, 62. Next, the proximity switches 68 are adjusted with respect to the slots 106 so that the case 28 is stopped at a position centered within the field of the lens 78 of the camera 80. The positions of the prism mounts 134 are adjusted together with the vertical positions of the camera 80 and the light 168, such that the camera 80 provides the desired images of the indicia 40, 42 on the respective ends 30, 36 and the indicia 44 of the upper surface 46 of the case 28.

The inspection controller 70 contains an Intelledex image processor commercially available from Vision Products, a division of Electro-Scientific Industries, Inc. of Wilsonville, Oreg. The image processor includes a monitor and mouse so that the camera images can be viewed and manipulated. Five of the cases 28 which are not defective and will provide the desired images on the edges 30, 36 and surface 46 are fed along the conveyor 24 into the inspection station 50. The leading edges of the cases are detected by the proximity switches 68, the camera is strobed ON and OFF to obtain the desired images of the case. The five good cases permit the camera 80 to produce five good images to the video processor in the inspection system controller 70 which stores an average of the five good images. Thereafter, the inspection station and conveyor are placed in a production mode in which cases are fed through the inspection station by the conveyor, which is operating approximately at a speed of 65 feet per minute.

As each case 28 enters the cabinet 56, the ends 100 of the guides 96 are effective to shift the case laterally with respect to the conveyor 24 to its desired position. When the leading edge 30 of the case is detected by the proximity switches 68, the camera 80 is strobed to receive the light 150 provided by the light source 168 and reflected from the ends 30, 36 and upper surface 46 of the case 28. The controller 70 processes that image and determines whether the case is to be accepted or rejected. That information is provided to other control systems so that the case 28 will be appropriately handled further down the conveyor line. For example, a cylinder (not shown) may be mounted on the edge of the conveyor at the output of the cabinet 56, and the controller 70, upon detecting that a case is to be rejected, actuates the cylinder to push the defective case laterally off of the conveyor into a collector.

The above inspection system 50 has a first advantage of being mounted at any location on a standard conveyor without requiring any adjustments or modifications to the conveyor. Further, the location of the inspection station may be easily changed by sliding the cabinet 50 in the slots 26 of the conveyor side rails 22. As a further advantage, the overall size of the inspection station 50 is minimal and consumes less than one foot of lineal conveyor space. In addition, the inspection system utilizes prism 60, 62, which have the advantage over mirrors in that they may be mounted in a static position above the case 28. The prisms 60, 62 permit the camera 80 to simultaneously inspect the top surface 46 and the ends 30, 36 of the case 28 while the conveyor is moving at its normal speed. Hence, the inspection process occurs without slowing or stopping conveyor and therefore, does not slow the overall packaging process.

While the invention has been illustrated by the description of one embodiment and while the embodiment has been described in considerable detail, it is not the intention to restrict or in any way limit the scope of the intended claims to such detail. Additional advantages and modifications will readily appear to those who are skilled in the art. For example, in the described embodiment, the light 168 operates continuously and the camera 80 is strobed. Alternatively, the light 168 may be strobed instead of the camera 80. Further, in some situations, depending on ambient light, the walls 128 may or may not be utilized. While the case 28 is preferably shown as moving along the conveyor with the hinge as the leading edge as will be appreciated, the case 28 may move along the conveyor with the end 36 leading and the hinged end 30 being the controlling edge. Similarly, the case 28 may be rotated 90° such that images of the opposite perpendicular ends may be inspected by the camera 80. In that situation, the guides 96 would have to be adjusted so that the ends 30, 36 could track between them. While in the disclosed embodiment, the case is transparent and the indicia are on a liner inside the case, the indicia may also be otherwise applied to the cases surfaces either by etching, printing or otherwise applying the indicia to one or more inner or outer surfaces of the case.

In a known manner, the inspection system controller 70 is preferably mounted on wheels and easily moved from one conveyor location to another. Further, the cable 69 is preferably connected to a connector on the cabinet 56 so that the controller 70 and cable 69 may be disconnected and moved independently of the cabinet 56.

The invention in its broadest aspects is, therefore, not limited to the specific details shown and described. Consequently, departures may be made from the details described herein without departing from the spirit and scope of the claims which follow.

What is claimed is:

1. A video inspection system for inspecting opposed first and second ends of a part moving on a continuously moving conveyor comprising:
   a frame adapted to be attached to the continuously moving conveyor;
   a video camera mounted on the frame above the part on the conveyor, the video camera having a light receiving lens;

a first prism mounted on the frame below the video camera and above the part to permit the part to pass on the conveyor below the first prism, the first prism having a longitudinal centerline extending substantially parallel to the first end of the part to be inspected, and the first prism having a surface oriented to reflect light from the first end into the lens of the video camera; and a second prism mounted on the frame below the video camera and above the part to permit the part to pass on the conveyor below the second prism, the second prism having a longitudinal centerline extending substantially parallel to the second end of the part to be inspected, and the second prism having a surface oriented to reflect light from the second end into the lens of the video camera, whereby the conveyor moves the part beneath the prisms to an inspection location between the prisms enabling the video camera to simultaneously provide images of the respective first and second ends.

2. The video inspection system of claim 1 wherein each of the first and second prisms is located adjacent one of the opposite ends of the part, the first and second prisms having respective longitudinal centerlines oriented substantially perpendicular to a direction of conveyor motion.

3. The video inspection system of claim 1 wherein the part has an upper surface and the video camera is mounted so that when the part is at the inspection location, light reflecting from the upper surface is directed into the lens of the video camera, and the video camera provides simultaneous images of the upper surface and the first and second ends of the part.

4. The video inspection system of claim 1 wherein a proximity sensor is mounted with respect to the conveyor to detect the presence of the part between the prisms and provide a signal commanding an operation of the video camera.

5. The video inspection system of claim 1 wherein the first and second ends of the part extend longitudinally in a direction substantially perpendicular to a direction of conveyor motion.

6. The video inspection system of claim 1 further comprising guides extending in a direction generally parallel to a direction of conveyor motion to align the part with respect to the video camera.

7. The video inspection system of claim 1 further comprising a housing for enclosing the video camera and the first and second prisms.

8. The video inspection system of claim 7 wherein the housing has opaque sides for preventing ambient light around the conveyor from entering the housing.

9. The video inspection system of claim 8 includes a movable cover on one side of the housing permitting access to an interior of the housing.

10. The video inspection system of claim 9 further comprising a source of light providing illumination in the interior of the housing.

11. A video inspection system for simultaneously inspecting an upper surface and opposed first and second end walls of a case moving on a continuously moving conveyor, the case having first and second indicia visible on the respective first and second end walls, the video inspection system comprising:

a frame adapted to be attached to structure of the continuously moving conveyor;

a video camera mounted on the frame above the part on the conveyor, the video camera having a light receiving lens; and first and second prisms mounted on the frame below the video camera and above the part to permit the part to pass on the conveyor below the prisms, the first and second prisms having respective longitudinal centerlines extending substantially parallel to the end walls of the part and substantially perpendicular to a direction of conveyor motion, the prisms being oriented to simultaneously direct images of the indicia on the end walls to the lens of the camera when the case is disposed on the conveyor below the camera and between the prisms.

12. The video inspection system of claim 11 wherein the part further has third indicia visible on the upper surface, and the video camera being mounted with respect to the part such that light reflected off of the upper surface of the part is directed into the lens.

13. A video inspection system for simultaneously inspecting an upper transparent surface and opposed first and second transparent end walls of a case moving on a continuously moving conveyor, the case having a liner with first and second indicia visible through the respective first and second end walls and third indicia visible through the upper surface, the video inspection system comprising:

a frame adapted to be attached to structure of the continuously moving conveyor;

a video camera having a light receiving lens and the video camera being mounted on the frame above the part such that an image of the third indicia visible through the upper surface of the part is directed into the lens;

first and second prisms mounted on the frame below the video camera and above the part to permit the part to pass on the conveyor below the prisms, the first and second prisms having respective longitudinal centerlines extending substantially parallel to the end walls of the part and substantially perpendicular to a direction of conveyor motion, the prisms being oriented to simultaneously direct images of the first and second indicia visible through the respective first and second end walls to the lens of the camera when the case is disposed on the conveyor below the camera and between the prisms; and a proximity sensor mounted with respect to the conveyor to detect the presence of the part between the prisms and provide a command signal commanding the video camera to simultaneously receive the images of the upper surface and the opposite ends of the part.

14. A method of simultaneously inspecting indicia on opposite ends of a case moving on a continuously moving conveyor comprising the steps of:

moving the case on the continuously moving conveyor below a video camera and two prisms, the prisms having a spaced apart relationship in the direction of conveyor motion;

moving the case to a position generally equally spaced between the two prisms such that light reflected off of the indicia on the ends of the case is directed toward a lens of the camera, the two prisms being mounted on a frame above the conveyor and below the camera and the frame being attached to structure of the conveyor; and operating the camera to simultaneously receive images of the indicia on the ends of the case.

15. The method of claim 14 wherein the case has indicia on an upper surface and the method further comprises:

moving the case to a position below the video camera such that light reflected off of the indicia on the upper surface of the case is directed toward a lens of the camera; and operating the camera to simultaneously receive images of the indicia on the ends of the case and the indicia on the upper surface.

* * * * *